Figure 1:
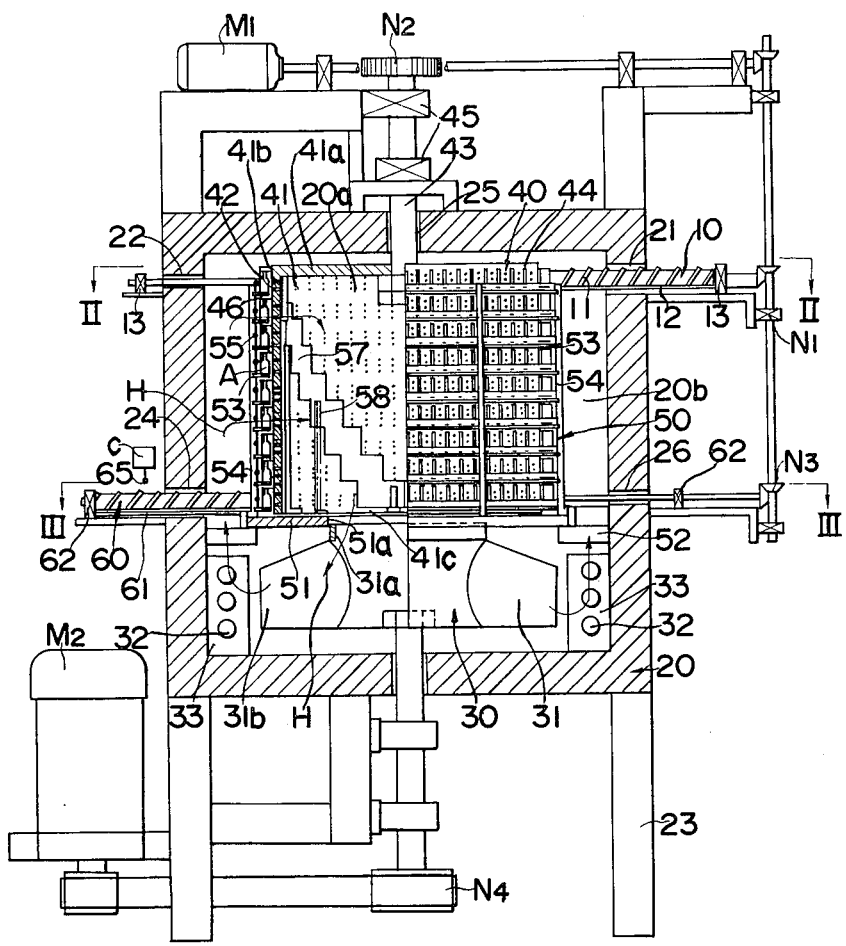

United States Patent [19]

Nagamatsu et al.

[11] 3,945,796

[45] Mar. 23, 1976

[54] APPARATUS FOR CONTINUOUS, AUTOMATIC STERILIZATION OF FLUID IN SEALED CONTAINERS

[75] Inventors: Kazuo Nagamatsu, Kobaya; Yoshitsugu Kinoshita, Osaka; Seizo Kawajiri, Kyoto; Yoshiaki Uda, Hyogo, all of Japan

[73] Assignee: Takeda Chemical Industries, Ltd., Osaka, Japan

[22] Filed: July 2, 1973

[21] Appl. No.: 375,475

[30] Foreign Application Priority Data

July 6, 1972 Japan.............................. 47-68082

[52] U.S. Cl. ........................ 21/80; 21/78; 198/104; 221/88; 432/144
[51] Int. Cl.² .................... A61L 3/00; B65G 37/00
[58] Field of Search ............. 21/78, 80; 221/79, 83, 221/88; 198/104, 136, 209; 34/236; 432/144–147

[56] References Cited
UNITED STATES PATENTS

| | | | |
|---|---|---|---|
| 2,549,216 | 4/1951 | Martin .................................. | 21/78 |
| 2,835,003 | 5/1958 | Abrams................................ | 21/78 |
| 3,058,732 | 10/1962 | Barnett et al. ....................... | 432/144 |
| 3,292,768 | 12/1966 | Matthews............................ | 198/104 |
| 3,606,997 | 9/1971 | Gackel................................. | 21/78 |

*Primary Examiner*—Barry S. Richman
*Assistant Examiner*—Dale Lovercheck
*Attorney, Agent, or Firm*—Wenderoth, Lind & Ponack

[57] ABSTRACT

An apparatus for sterilization of fluid in sealed containers such as ampoules, the apparatus has a chamber provided with a hot air distributor therein, a magazine conveyor comprising a drum mounted to be rotable about its vertical axis in said chamber having compartment defining means thereon defining a plurality of vertically stacked tiers of compartments for accomodation and transportation of containers to be treated, said chamber having a plurality of bottom walls fixedly mounted therein one being associated with each tier of compartments and constituting the bottoms of said compartments each bottom wall having a gap therein, the gaps being at different circumferential positions, the gaps being for transferring containers inserted and carried in compartments automatically one after the other to the next adjacent lower tier at said positions, one wall of each compartment permitting passage of air therethrough and apparatus for supply and removal of containers to be treated to and from said magazine conveyor, whereby hot air is constantly circulated and recirculated around containers to be treated carried on said magazine conveyor for sterilizing fluid contained in the sealed containers.

5 Claims, 15 Drawing Figures

APPARATUS FOR CONTINUOUS, AUTOMATIC STERILIZATION OF FLUID IN SEALED CONTAINERS

The present invention relates to an apparatus for continuous, automatic sterilization of medicinal or other fluid in sealed containers such as ampoules or phials.

A conventional method of sterilizing medicinal fluid in sealed containers depends essentially on the use of heated steam. This method has disadvantages with respect to operation and also it is often the source of undesirable side effects in the fluid being sterilized. Fluid contained in sealed containers must be subjected to a temperature of 100° C for 60 minutes or to a temperature of 120° C for 20 minutes, and because of the length and severity of this heat treatment there are frequently compositional changes, discoloration or precipitiation of dissolved elements in the fluid treated. Also, to bring the temperature of the steam in the sterilization chamber to a temperature at which sterilization is effective, the pressure of the steam (saturation pressure) must be about 2 kg/cm$^2$, with the result that execution of this method can be dangerous, and also that continuous, automatic operation is comparatively difficult to attain.

Other conventional methods for the sterilization of medicinal or other fluids in sealed containers involve irradiating the fluid with ultrasonic rays, ultraviolet rays or other forms of radiation. But these methods often have adverse effects on the characteristics of treated fluids and also are dangerous to the attendant workers.

It is accordingly an object of the present invention to provide an apparatus for continuous, automatic sterilization of medicinal or other fluids contained in sealed containers such as ampoules or phials which does not present any dangers in operation and is not the source of adverse effects on treated fluid or on attendant persons or workers.

According to the present invention, there is provided a multi-tiered magazine conveyor on each tier of which there is a plurality of suitably spaced compartments for holding sealed ampoules or phials or similar containers (below referred to as 'ampoules' for the sake of brevity) containing medicinal or other fluid (below simply referred to as 'fluid'). The magazine conveyor is housed within a substantially, hermetically sealed chamber equipped with a hot air distributor for the sterilization of fluid in the ampoules. Ampoules are supplied to the top tier of the magazine conveyor by a supply conveyor external to the sterilization chamber, and are removed from the bottom tier by a discharge conveyor, also external to the sterilization chamber. Ampoules are carried round the tiers of the magazine conveyor. In each tier except the bottom tier, as each ampoule comes to a certain point, it passes through a hole or a split portion formed in the support base of the tier and moves down to the next lower tier. After being carried around the bottom tier, ampoules are removed by the discharge conveyor. The hot air distributor continuously circulates and recirculates hot air around the sterilization chamber. In this equipment, the supply and discharge conveyors and the magazine conveyor are driven synchronously. This can be achieved, for example, by a single motor acting through suitable gears or transmission elements, and so once ampoules are supplied to the supply conveyor the whole operation is continuous and automatic. The central portion of the magazine conveyor is hollow, and there are holes formed in the ampoule carrier compartment walls adjacent to the central portion. Also, ampoules are kept separated from the compartment walls at a suitable distance, which is generally about 0.5–1.5 mm, to permit a flow of air around the sterilization chamber and around the ampoules in the magazine conveyor compartments through holes at a velocity of about 30–40 m/sec. Fluid in ampoules carried by the magazine conveyor is sterilized by the heat of the air circulated by the distributor. Since this air is constantly circulated around the sterilization chamber and through the magazine conveyor, and the ampoule carrier compartments, the temperature can be easily adjusted, and fluid can be brought to a suitable temperature for sterilization. A suitable temperature is between about 120°–200° C, and ampoules can be carried through the process in a time short enough to ensure that there are no changes in the characteristics of the fluid treated.

The invention offers the advantages that since sterilization of fluid is effected by hot air, the process is clean, and, unlike conventional methods using steam, or ultrasonic, ultraviolet or other forms of radiation, there are no dangerous pressures and the process does not present a health hazard for personnel.

Also, according to the invention, since the ampoule carrier compartments of the magazine conveyor are spaced at predetermined intervals and there are holes in the compartment walls, there is a free flow of air around the magazine conveyor, the ampoules carried thereon and within the sterilization chamber. Therefore, there is an even distribution of temperature, and there is no risk of some ampoules being exposed to high temperature. The holes in the compartment walls can of course be of any size. Generally, the larger the holes, the better the distribution of air. Also, there may be a number of holes in one compartment wall.

A further advantage of the invention is that, since ampoules are carried in separate compartments on the magazine conveyor, even if an ampoule shatters, other ampoules are not damaged since they are protected by the compartment walls.

Another advantage is that pressure rises within the sterilization chamber can be prevented by making the magazine conveyor a vertical rotary magazine conveyor, and drawing heated air from the portion of the chamber outside the conveyor, through the conveyor compartments and into the conveyor central portion. In other words, pressure inside the chamber can be kept at atmospheric pressure, and even without provision of an air seal there is no leakage of air when ampoules are brought into or removed from the chamber.

In one preferred embodiment of the invention, the magazine conveyor is made a vertical rotary magazine conveyor which has a number of tiers, each of which is provided with a plurality of compartments for carrying ampoules. Ampoules are supplied to the top tier by a supply conveyor and removed from the bottom tier by a discharge conveyor. Each tier comprises a stationary baseboard, above and on which are rotated compartments for carrying ampoules. At a set point in the baseboard of each tier there is formed a hole or a split portion large enough to permit the passage of an ampoule. Ampoules inserted in compartments are carried around the baseboard of each tier, and when they come to the hole or split portion in the baseboard, they fall through to a compartment in the next lower tier. This embodiment provides a large capacity for ampoules to be treated since there is a plurality of tiers in the magazine conveyor.

Figure 6:
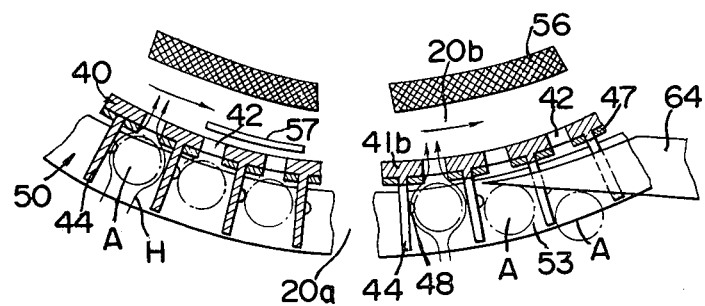
Figure 2:
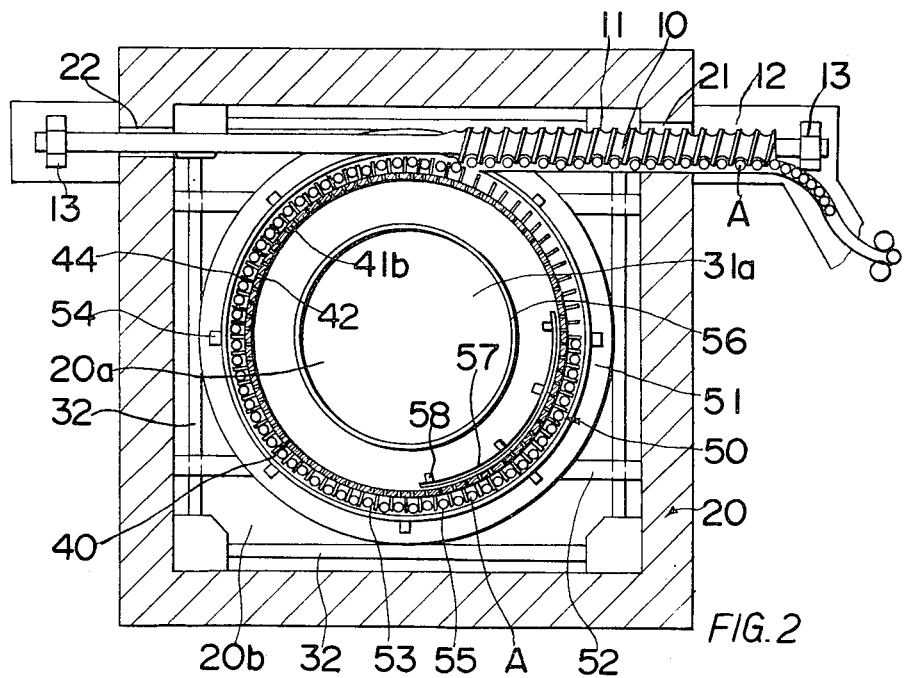
Figure 3:
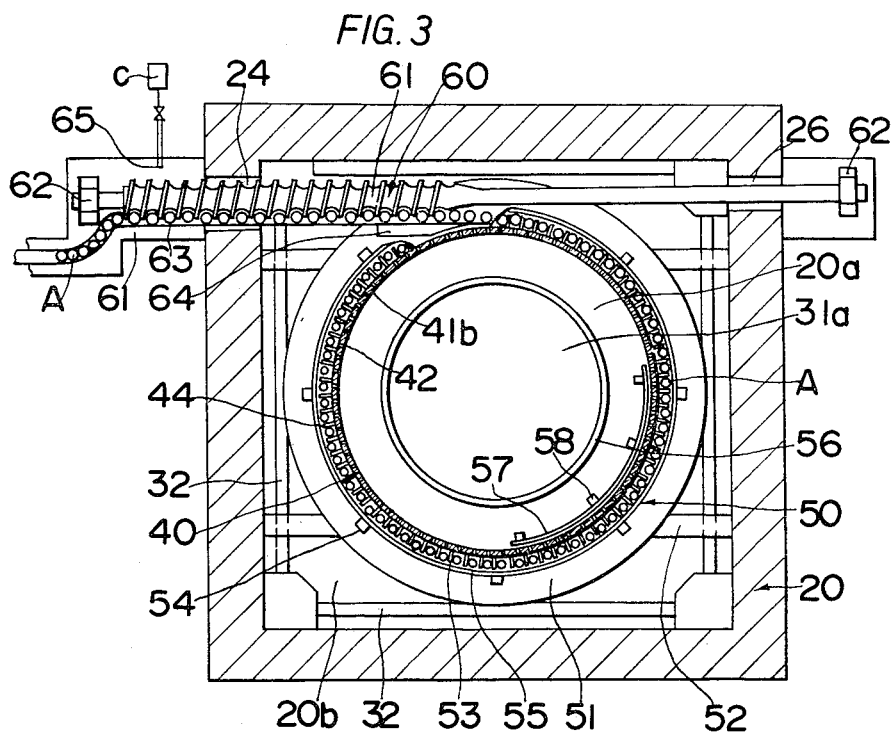
Figure 4:
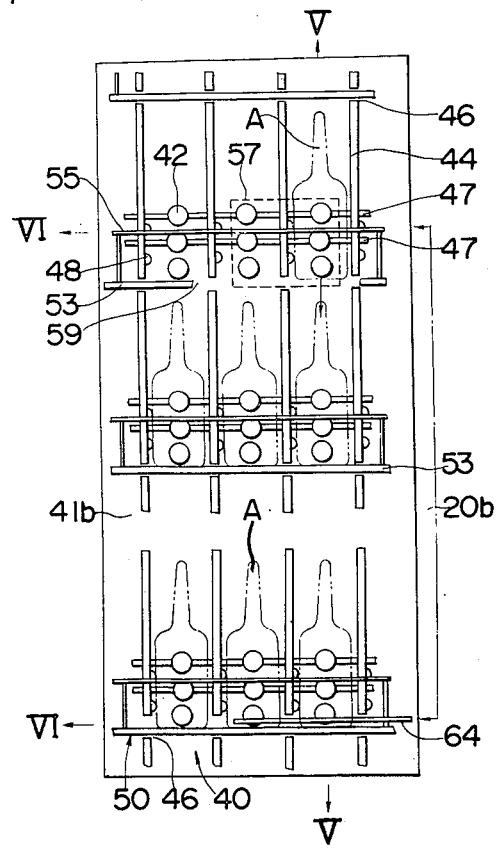
Figure 5:
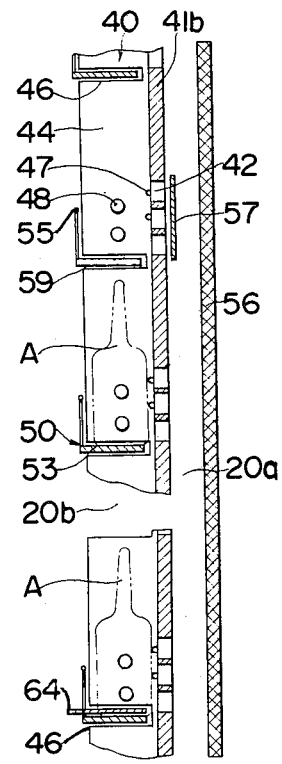
Figure 7:
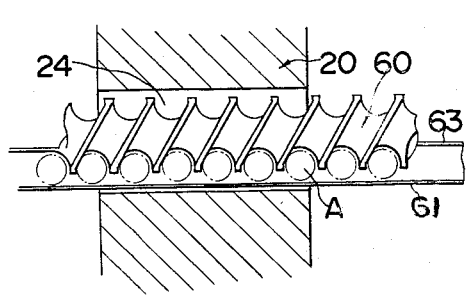
Figure 8:
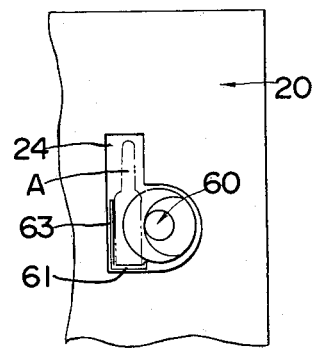
Figure 9:
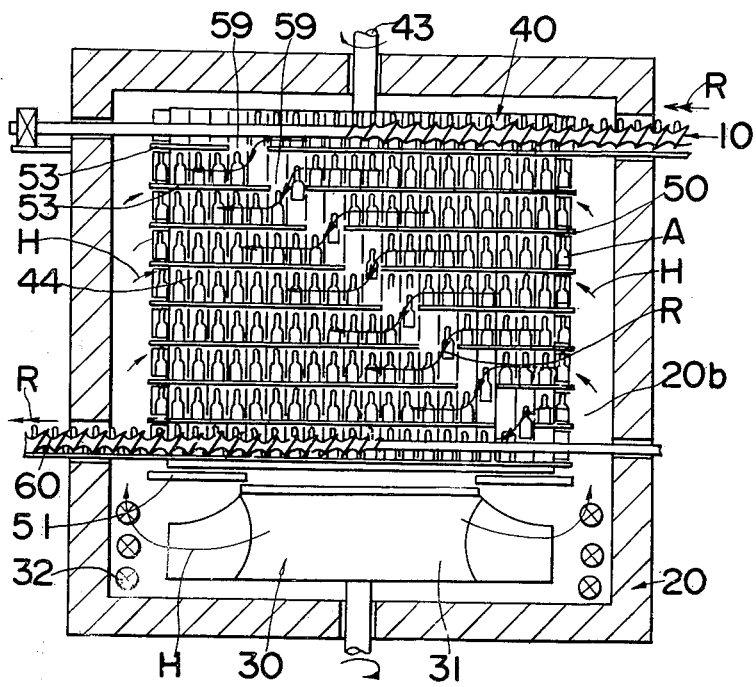
Figure 10:
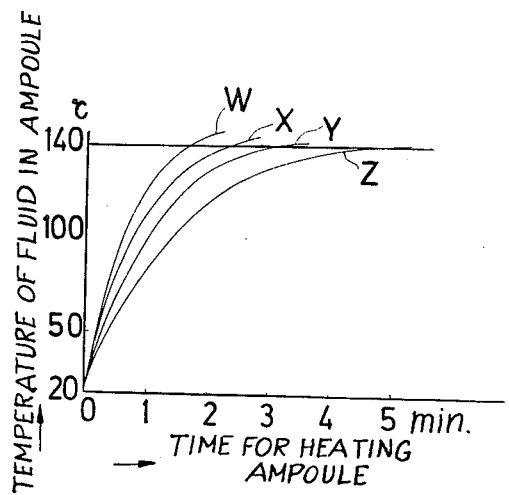
Figure 14:
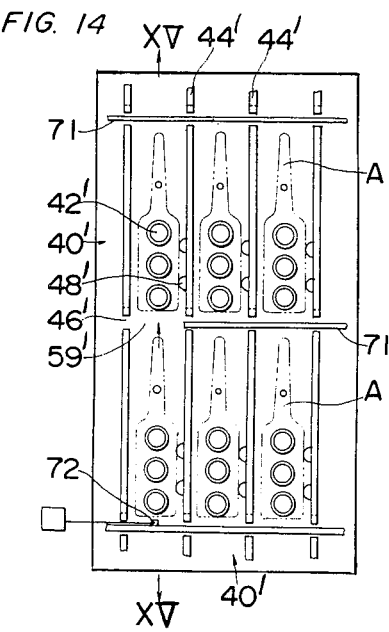
Figure 13:
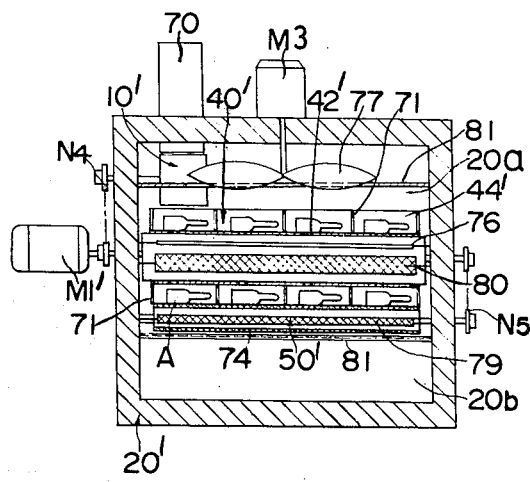
Figure 15:
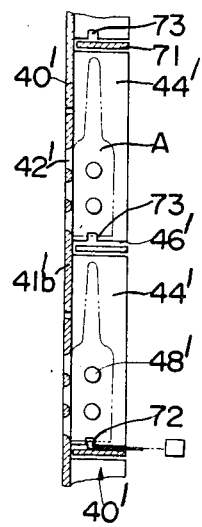
Figure 11:
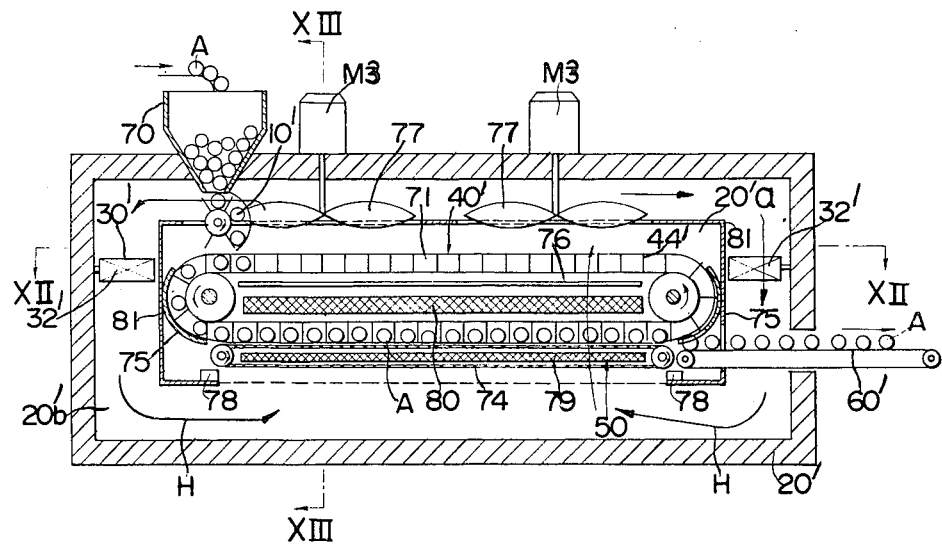
Figure 12:
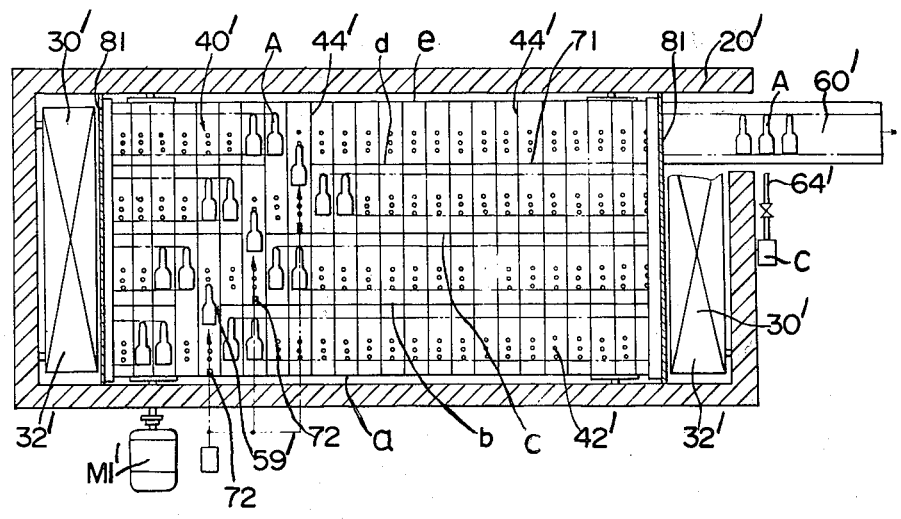

In another embodiment of the invention, the magazine conveyor is a conveyor which carries ampoules in rows in the same direction and in the same plane. Ampoules are supplied at one end of the conveyor, to the first row and removed from the other end of the conveyor, from the last row. Ampoules are transferred from one row to another by compressed air from a blower nozzle, or similar means. The means according to this second embodiment is also simple in construction and of large capacity. These and other objects and features of the present invention will become apparent from the following description taken in conjunction with the preferred embodiments thereof with reference to the accompanying drawings, in which;

FIG. 1 is a side sectional view of an apparatus for sterilization of fluid in sealed ampoules according to one preferred embodiment of the present invention, FIG. 2 is a cross sectional view taken along the line II—II in FIG. 1, FIG. 3 is a cross sectional view taken along the line III—III in FIG. 1, FIG. 4 is a front elevational view, on an enlarged scale, showing a portion of the ampoule carrier compartments of FIG. 1, FIG. 5 is a side sectional view taken along the line V—V in FIG. 4, FIG. 6 is a cross sectional view taken along the line VI—VI in FIG. 4, FIG. 7 is a cross sectional view, on an enlarged scale, showing a portion of a discharge screw passing through a chamber opening of FIG. 1, FIG. 8 is a side elevational view of FIG. 7, FIG. 9 is a rear elevational view showing ampoule carrier compartments for the purpose of illustrating the transport of ampoules in FIG. 1, FIG. 10 is a graph showing relation between fluid temperatures in a sealed ampoule and times for holding the ampoule in the a sterilization chamber of FIG. 1, FIG. 11 is a similar view to FIG. 1, but showing the apparatus according to the second preferred embodiment of the present invention, FIG. 12 is a cross sectional view taken along the line XII—XII in FIG. 11, FIG. 13 is a cross sectional view taken along the line XIII—XIII in FIG. 11, FIG. 14 is a front elevational view, on an enlarged scale, showing a portion of the ampoule carrier compartments of FIG. 11, and FIG. 15 is a cross sectional view taken along the line XV—XV in FIG. 14.

Before the description of the present invention proceeds, it is to be noted that like parts are designated by like reference numerals throughout the accompanying drawings. It is further to be noted that the present invention is hereinafter described as applied in sterilizing medical solution in sealed ampoules.

The ampoule sterilizing apparatus according to the present invention comprises, as shown in FIG. 1, a feeder unit including a screw conveyor 10; a sterilizing unit including a chamber 20 and a hot air distributor 30; a transport unit accomodated in the chamber 20 and including a rotatory magazine conveyor 40 and stationary elements 50; and a removal unit including a screw conveyor 60.

The screw conveyor 10 in the feeder unit may be of any known type and includes screw conveyor helixes 11 having a pitch substantially equal to the outer diameter of each ampoule A. This screw conveyor 10 is used to supply one after another a plurality of ampoules placed on a suitable tray 12, which may otherwise be in the form of an endless belt conveyor or any other cage, to the rotatory magazine conveyor 40 through an opening 21 of the chamber 20. The screw conveyor 10 is driven by an electrical motor $M_1$ through gear transmission mechanism $N_1$ at a speed preselected as will be described later.

The screw conveyor 10 extends horizontally in parallel to the top disk 41a of a magazine conveyor drum 41 and both ends of the screw conveyor 10 are situated outside the chamber 20 through the openings 21, 22, which are formed in the opposed walls defining said chamber 20, while substantially all the intermediate portion of the screw conveyor 10 is situated within said chamber 20. Also, the screw conveyor 10 is supported at both ends by bearings 13, provided outside the chamber 20, and has the helix 11 from its one end extended outside the chamber 20 to its intermediate portion in the chamber 20, the inner end of which faces to the upper portion of the outer periphery of the magazine conveyor side wall 41b so as to supply an ampoule A from the screw conveyor 10 to the magazine conveyor 40.

The chamber 20 is a cubic container made of adiabatical materials with legs 23, and accomodates the hot air distributor 30 and transport unit therein. A pair of openings 21 and 24 each having a cross section of a shape of a figure "b", as shown in FIGS. 7 and 8, are provided respectively at upper portion of the right side wall and at lower portion of the left side wall of the chamber 20 for passing through the screw conveyors 10 and 60 together with ampoules A. The shapes of openings 21 and 24 are made just big enough to pass the screw conveyor 10 or 60 and an ampoule A transferred by the screw conveyor along tray 11 or 61, without permitting air to flow into and out from the chamber 20.

The rotatory magazine conveyor 40 comprises a cap-like drum 41 having a top disk 41a and a cylindrical side wall 41b with holes 42 for flowing air from the outside into the inside by means of the hot air distributor 30 as described later, a drive shaft 43 extending from the center of the top disk 41a for rotating the drum 41, and a plurality of partition plates 44 disposed at equal intervals, each of which is sufficient to accomodate the width of an ampoule A, around the outer periphery of the side wall 41b and extending radially outwards therefrom in the direction of the length of the side wall 41b, both the shaft 43 and plates 44 being arranged in parallel to the axis of the drum 41. The drum 41 is accomodated in the chamber 20 and is suspended from the upper wall of the chamber 20 by means of the drive shaft 43, one end of which is extends outside the chamber 20 through an opening 25 formed in the upper wall of the chamber 20 and is supported by bearings 45 provided on the chamber 20. The chamber 20 is thus divided into two main portions, which are a central chamber 20a inside the drum 41, and an outer chamber 20b outside the drum 41. The drive shaft 43 is driven by the motor $M_1$ which acts through a transmission element $N_2$ to which the upper end of the drive shaft 43 is connected, so that the magazine conveyor 40 formed of the side wall 41b and partition plates 44 is driven in rotatory motion by the drive shaft 43.

There is provided at least more than one slot 46 in each partition plate 44 at equal intervals, each of which is sufficient to accomodate the height of an ampoule A, all of slots 46 next to each other being arranged in one circle on a supposed horizontal plane. Perpendicular to the axis of the drum 41. The radial dimension of the partition plates 44 is slightly greater than the width of the ampoule A while the depth of the slots 46 cutout from the outside of the partition plates is slightly smaller than the radial dimension of the partition plates 44.

The stationary elements 50 comprise an annular support 51 fixedly mounted in the chamber 20 by stays 52 so as be positioned horizontally under the drum 41 with a little gap for making the lower opening 41c of the drum 41 narrow, a plurality of annular baseboards 53 mounted horizontally on struts 54, which are fixedly provided on the annular support 51, in concertric relation to the annular support 51 at equal intervals corresponding to those of the slots 46 of the partition plates 44 so as to form a staircase of steps for standing ampoules A thereon, guide rings 55 optionally provided over the annular baseboards 53 for preventing an ampoule from falling, a cylindrical screen 56 optionally provided on the annular support 51 in the drum 41 for stopping ampoule's fraction, and windbreaks 57 mounted behind the holes 42 of the drum 44 on poles 58 mounted on the annular support 51 in the drum 41 for opposing air flow passing through the holes 42. The baseboards 53 surround the outer periphery of the side wall of drum 41, and each inner portion of the baseboards 53 is inserted into the slots 46 of the partition plates 44 arranged in one circle with a little gap therebetween, the width of the baseboards being sufficient to support ampoules A thereon. The outer surface of the side wall 41b, and a pair of the partition plates 44, and the baseboards 53, thus form one compartment with one open side facing outwardly, into which an ampoule A may be inserted. Also, the baseboards 53 divide the magazine conveyor 40 into a number of separate tiers along the axial direction of the drum 41. In each tier, when the magazine conveyor 40 is driven to rotate in one direction by the drive shaft 43, an ampoule A inserted in a compartment is pushed by one partition plate 44 and slides along a baseboard 53.

The ampoule carrier compartments are shown in further detail in FIGS. 4 to 6. In these drawings it will be seen that in each compartment there are formed three holes 42 in the side wall 41b of the drum 41. The holes 42 provide a passage for air from the outer chamber 20b to the central chamber 20a through the compartment. In each compartment the holes 42 are formed slightly above the baseboard 53, in other words, approximately opposite the body of an ampoule A inserted in the compartment. In order to ensure that ampoules A do not block the holes 42, each compartment is provided with a pair of rails 47 which extend outwardly from the side wall 41b and prevent the body of an ampoule A from coming into direct contact with the wall 416 around the holes 41. Also, to ensure that air is able to flow completely around ampoules A in compartments, in each compartment the partition plate 44 which pushes an ampoule A when the magazine conveyor 40 is rotated, is provided with projections 48, which prevent the body of the ampoule A coming into direct contact with that partition plate 44. To prevent ampoules A from falling from the compartments, it is preferable to further provide guard rings 55 extending vertically upwards from the outer edge of the baseboards 44. At a certain location in each baseboard 53 there is formed a split gap 59, the ends of which are positioned near the partitition plates 44 and the length of which is approximately twice that of a compartment. In addition, holes 42 of the drum 41 to be positioned in the compartment having the split portion 59 are covered by the windbreaks 57 provided opposite the inner surface of the drum 41, thereby to cause to oppose flow of air through the holes 42. Each gap 59 in each baseboard 53 is in a different location, that is, the gaps 59 are not vertically aligned with one another. As described above, an ampoule A is carried in a compartment by being pushed by a partition plate 44 and slid along a baseboard 53. When an ampoule A thus carried is brought to the gap 59 of a baseboard 53, it falls through the gap 59 onto the next lower tier and is then carried in a compartment of the next tier. In this manner, an ampoule is carried in a compartment in each tier while it falls from one tier to another tier through a gap. Ampoules A are supplied to the top tier of the magazine conveyor 40 by the supply screw conveyor 10, and removed from the bottom tier of the magazine conveyor 40 by the discharge screw conveyor 60. Ampoules A are fed to the supply conveyor 10 from a feed table (not shown in Figures) external to the chamber 20, and the supply conveyor 10 passes horizontally through the opening 21 in a side wall of the chamber 20 level with the top tier of the magazine conveyor 40. The discharge conveyor 60 of the removal unit lies level with the bottom tier of the magazine conveyor 40 and extends horizontally through an opening 24 in a side wall of the chamber 20, to carry ampoules A to the next process. Both ends of the discharge conveyor 60 are situated outside the chamber 20 through the openings 24 and 26 which are formed in the opposite walls of the chamber 20 and supported by bearings 62, 62 provided outside chamber 20, and the substantially all the intermediate portion of the discharge conveyor 60 is situated within the chamber 20, the screw helix of the discharge conveyor 60 extending from the intermediate portion to the one end. In addition, there is provided a tray 61 beneath the discharge conveyor 60, a guide rail 63 extending vertically upwards from the outer edge of the tray 61 in front of the discharge conveyor 60, and a removing board 64 provided in the lowest slot 46 of the plates 44 at a position near the outer periphery of the magazine conveyor 40 by which ampoules A held in compartments of the magazine conveyor 40 are guided as they are taken out of the magazine conveyor 40 and, then, received by the discharge conveyor 60.

The drive shafts of the screw conveyors 10 and 60 are driven through coupling gears $N_1$ and $N_3$, which are connected to the transmission element $N_2$, in a known manner. In other words, the conveyors 10 and 60 are driven by the same motor $M_1$ that drives the magazine conveyor 40, and operation of the conveyors 10, 40 and 60 is completely synchronized. When the motor $M_1$ is started, the magazine conveyor 40 turns and the supply conveyor 10 feeds successive ampoules A into successive compartments in the top tier of the magazine conveyor 40, as shown by arrows R in FIG. 9. As the magazine conveyor 40 turns, each ampoule A is brought to the gap 59 in the baseboard 53 of the top tier, and falls through the split portion 59 into a compartment of the next lower tier. The ampoule A is then carried around the 2nd tier until it is brought to the gap 59 in the baseboard 53 of the 2nd tier, and falls into a compartment of the 3rd tier, and so on, until it reaches the bottom tier. When the ampoule A carried around the bottom tier is brought into direct contact with and is guided by the removing board 64, it comes to the intermediate portion of the discharge conveyor 60, which removes the ampoule A from the chamber 20, to the next process. Provided below the magazine conveyor 40 and in the outer chamber 20b there is the hot air distributor 30 comprising a distributor 31 and heaters 32. The distributor 31 may be a turbo-fan of any known type such as Silocco fan, and the suction portion 31a thereof is slidably fitted into the inner opening 51a of the annular support 51 through a Labyrinth packing (not shown in figures). The distributor 31 is driven through a transmission element $N_4$ by a motor $M_2$ situated outside the chamber 20. Heaters 32 also are provided on stays 33 in front of the injection portion 31b of the distributor 31 in the lower part of the outer chamber 20b. Hot air being produced by the hot air distributor 31 circulates in the chamber 20, and ampoules A carried by the rotatory magazine conveyor 40 are sterilized by the hot air passing around the outer periphery thereof, as shown in FIG. 6. The circulatory path of air driven by the hot air distributor 30 is, as shown by arrows H in FIG. 1 from the outer chamber 20b into the compartments for ampoules through the holes 42, into the central chamber 20a, to the distributor 30, past the heaters 32, and then again into the compartments. Ampoules A carried by the magazine conveyor 40 are thus evenly heated by a constant flow of hot air. As described earlier, if an ampoule A shatters by accident, other ampoules A are not effected since they are protected by the side walls 41b of the compartments. In order to prevent fragments of shattered ampoules A entering the central chamber 20a, there may be optionally provided a cylindrical screen 56 inside the side wall 41b of the magazine conveyor 40. Any remnants of shattered ampoules A that are carried out of the chamber 20 by the discharge conveyor 60, are removed by compressed air from a nozzle 65. The nozzle 65 is situated adjacent to the conveyor 60 immediately on the exit side of the chamber 20, and directs thereon compressed air C with sufficient force to dislodge any ampoule fragments that may be carried by the conveyor 60. The force of the compressed air from the nozzle 65 is not, however, sufficient to move an ampoule A filled with fluid, and so whole ampoules A pass by the nozzle 65 unaffected. As a further check that ampoules A coming from the chamber 20 are satisfactory, the conveyor 60 carries the ampoules A to the guide rail 63, which tilts the ampoules A so that it may be observed whether there is any leakage of fluid therefrom. After this, ampoules A are restored to an upright position and carried to the next process. With the apparatus of the present invention being constructed as above described, fluid contained in sealed ampoule A is sterilized by hot air of high temperature, for example, 150° C and of high velocity, for example, 81 m/sec. (W), 40 m/sec. (X), 19 m/sec. (Y). 10 m/sec. (Z). produced by the hot air distributor 30 during which the ampoule A stays in the chamber 20, as shown in FIG. 10. It is to be noted that the higher the velocity and the temperature of the hot air, the shorter the time until the fluid of ampoule attains a predetermined temperature T. Also, the above mentioned factors of hot air and time for treatment of ampoules may be suitably selected in accordance with the kind and volume of fluid contained in the sealed ampoules.

In another embodiment of the invention, which is shown in FIGS. 11 to 15, the magazine conveyor 40' is not a vertical, but a horizontal type. In addition, the supply conveyor is in the form of a vaned wheel 10', and the discharge conveyor 60' is a belt conveyor. Also, ampoules A are fed to the supply conveyor 10' through a hopper 70.

As in the 1st embodiment, the magazine conveyor 40' is provided with a plurality of compartments for transport of ampoules A. But in the 2nd embodiment the compartments are disposed in rows on the same plane of the magazine conveyor 40'. The compartments are formed by a pair of orthotomic walls 44' and 71 which extend vertically outwards at equal intervals with respect to the surface of the magazine conveyor 40'. The walls 44' are disposed transversally across and fixedly on the surface of the magazine conveyor 40'. The other walls 71 are made of annular plates fixedly disposed longitudinally with respect to the magazine conveyor 40', that is at right angles to the walls 44', and slidably inserted into slots 46' provided on the first mentioned walls at equal intervals. The walls 71 of the 2nd embodiment correspond to the baseboards 53 in the 1st embodiment, but divide the compartments into rows instead of into tiers. Ampoules A are supplied to the first row, at one end of the magazine conveyor 40', carried round the conveyor 40', transferred to the next row, in a manner described below, transferred to and carried round in successive rows and finally removed from the last row, from the opposite end of the conveyor 40' to the supply end.

In each wall 44', and 71 there are slots at the locations of the other walls 71 and 44', whereby the walls 44' may be moved without hindrance when the conveyor 40' is rotated. In a set location in each wall 71 except the two walls 71 lying immediately adjacent to the outer edges of the conveyor 40' there is a gap 59'. The gap 59' in the different walls 71 are not aligned with one another. A compressed air nozzle 72 is positioned on each wall 71 opposite the gap 59' in the succeeding wall. That is, if, for example, there are five walls 71 (and therefore four rows of compartments), and if from the first to the last row the walls 71 are considered as wall a, wall b, wall c, etc., as shown in FIG. 12, the compressed air nozzle 72 on wall a is positioned opposite the gap 59' in wall b, the compressed air nozzle 72 on wall b is positioned opposite the gap 59' in wall c, and so on. When an ampoule A in a compartment is carried into line with a nozzle 72 the compressed air therefrom pushed the ampoule A into the next succeeding row. Notches 73 are cut at the bottom of sections of the walls 44' which form the sides of a compartment, and which pass over nozzles 72, to permit the conveyor 40' to rotate freely.

Underneath the magazine 40' there is provided a support 74 in the form of a net conveyor with permeability running in the same direction as the magazine conveyor 40', in order to prevent ampoules A from falling. In this embodiment, the vaned wheel 10', magazine conveyor 40', discharge conveyor 60' and net conveyor 74 are driven synchronously by means of transmission elements $N_4$ and $N_5$ and motor $M_1'$. There are also provided guide boards 75 at the ends of the magazine conveyor 40, to prevent ampoules from falling when they are carried around the ends of the conveyor 40'. The guide board 75 does not however cover the discharge end of the last row, from which ampoules are removed by the belt conveyor 60'.

In the 2nd embodiment, as well as heaters 32' in the chamber 20', there is also provided a supplementary heater 76, which is in the form of a hot air blower, and which is positioned below the top side of the conveyor 40'. Also, two fans 77 driven by motors $M_3$ are provided above the conveyor 40'. Below both ends of the magazine conveyor 40' there are provided boxes 78 into which fragments of broken ampoules A may fall through gaps between the guide boards 75 and the support 74. In each space between the upper and lower portions of the conveyors 40' and 74 there is respectively provided a plane screen 79, 80 for stopping ampoules' fraction. Also, there are provided parting strips 81 between the heaters 32' and the conveyors 40', 74 to guide hot air from the upperside of the fan 77 to the underside of the conveyors 74. Hot air produced by means of the fan 77 and heaters 32', is circulated in the chamber for sterilizing fluid contained in sealed ampoules carried by the conveyors 40'. The circulatory path of hot air driven by the fan 77 is, as shown by arrows H in FIG. 11, from the outer chamber 20b outside the parting strip past the underside of the conveyor 74, into compartments of two steps on the magazine conveyor 46, through the holes provided in the magazine conveyor 40', the screens 79, 80 and the supplementary heater 76, to the fan 77, past the heaters 32', the net conveyor 74, and again into the compartments. As may be seen from the above description, the present invention provides an apparatus for sterilization of fluid in small containers, which is rapid, continuous, and automatic.

The present invention has been fully disclosed by way of the preferred embodiments thereof. However, it is to be noted that various changes and modifications thereof are apparent to those skilled in the art from the foregoing description with or without reference to the accompanying drawings. Therefore, these and other changes and modifications should be construed as included within the scope of the present invention unless otherwise departing therefrom.

What is claimed is:

1. An apparatus for sterilization of fluid of sealed containers, comprising a chamber substantially hermetically sealed and having a supply point at one part of said chamber at which is a supply opening in said chamber land having a removal point at another part of said chamber spaced from said supply point and at which is a removal opening, means for supply of containers to be treated extending from the outside of said chamber to the supply point through the supply opening of the chamber, means for removal of treated containers extending from the removal point to the outside of the chamber through the removal opening of the chamber, drum mounted to be rotatable about its vertical axis in said chamber having compartment defining means thereon defining a plurality of vertically stacked tiers of compartments for accommodation and transport of containers to be treated, said chamber having a plurality of bottom walls fixedly mounted therein one being associated with each tier of compartments and constituting the bottoms of said compartments, each bottom wall having a gap therein, the gaps being at different circumferential positions, the gaps being for transferring containers inserted and carried in compartments automatically one after the other to the next adjacent lower tier at said positions, means in said chamber for heating air and circulating the heated air in the chamber, each compartment having aperture means therein for permitting passage of the circulating hot air laterally therethrough in a direction transverse to the direction of transport of the containers for sterilizing the fluid contained in the containers, and drive means connected to said conveyor for continuously driving the conveyor to carry the containers within the compartments from the supply point to the removal point, said drive means, supply means and removal means being coupled for synchronous driving.

2. An apparatus as claimed in claim 1 wherein said air heating and circulating means comprises a distributor for circulating air and a heater over which the air being circulated is caused to flow.

3. An apparatus as claimed in claim 1 wherein said supply means comprises a conveyor moving from the outside of the chamber to the inside of the chamber by which a container carried by the supply means is transferred to the rotatable drum.

4. An apparatus as claimed in claim 1 wherein said removal means comprises a conveyor moving from the inside of the chamber to the outside thereof by which a container carried by the rotatable drum is transferred to the outside of the chamber.

5. An apparatus for sterilization of fluid in sealed containers, comprising a chamber substantially hermetically sealed and having a supply point at one part of said chamber at which is a supply opening in said chamber and having a removal point at another part of said chamber spaced from said supply point at which is a removal opening, means for supply of containers to be treated extending from the outside of said chamber to the supply point through the supply opening of the chamber, means for removal of treated containers extending from the removal point to the otuisde of the chamber through the removal opening of the chamber, a magazine conveyor in said chamber constituted by a cylindrical drum means, a means rotatably mounting said drum within the said chamber, a plurality of partition plates disposed at equal intervals around the outer periphery of the drum and extending radially outwardly therefrom, a plurality of baseboards fixedly mounted in position within said chamber in planes transverse to the axis of said drum at intervals along said drum axis, said partition plate shaving slots therein in a direction transverse to the axis of the drum and into which said baseboards extend in slidable relationship, said partition plates and baseboards and the outer peripheral surface of the drum constituting vertically stacked tiers of compartments for carrying containers, and each baseboard having a gap therein for passing a container therethrough to the next adjacent lower tier, one portion of the periphery of the drum being at the supply point and another portion of the periphery of the drum being at the removal point, means in said chamber for heating air and circulating the heated air in the chamber, the wall of the drum in each compartment having at least one aperture therein for permitting passage of the circulating hot air laterally therethrough in a direction transverse to the direction of transport of the containers for sterilizing the fluid contained in the containers, and said rotatable mounting means includes drive means for continuously rotating the drum to carry the containers within the compartments from the supply point to the removal point, said drive means, supply means and removal means being coupled for synchronous driving.

\* \* \* \* \*